US00PP12058P2

(12) United States Plant Patent
VandenBerg

(10) Patent No.: US PP12,058 P2
(45) Date of Patent: Aug. 14, 2001

(54) CHRYSANTHEMUM PLANT NAMED 'HONEY YOGILROY'

(75) Inventor: Cornelis P. VandenBerg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/383,535

(22) Filed: Aug. 26, 1999

(51) Int. Cl.[7] ..... A01H 5/00
(52) U.S. Cl. ..... Plt./289
(58) Field of Search ..... Plt./289, 290

(56) References Cited

PUBLICATIONS

Datta, 1994, "Sensitivity of Mutant Genotype of Chrysanthemum to Gamma Rays", J. Nuclear Agric. Biol., 23(4):251–254.*
"Mutation Studies on Chrysanthemum", NBRI Newsletter, 1989, 16(1):2–3.*
Datta, 1991, "Evaluation of Recurrent Irradiation on Vegetatively Propagated Ornamentals: Chrysanthemum", J. Nuclear Agric. Biol., 20(2):81–86.*
Banerji, et al., 1990, "Induction of Somatic Mutation in Chrysanthemum Cultivar 'Anupam'", J. Nuclear Agric. Biol., 19:252–256.*
Datta, 1985, "Gamma Ray Induced Mutant of a Mutant of Chrysanthemum", J. Nuclear Agric. Biol., vol. 14: 131–133.*
Gosling, ed., 1979, "The Chrysanthemum Manual—6th Edition", The National Chrysanthemum Society, Essex Telegraph Press, Ltd., London, pp. 329–336.*
Broertjes, et al., 1978, "Application of Mutation Breeding Methods in the Improvement of Vegetatively Propagated Crops", Elsevier Sci Pub. Co., New York, pp. 162–175.*
Gupta, et al., 1978, Mutation Breeding of Chrysanthemum. II. Detection of Gamma Ray Induced Mutations in vM2, J. Nuclear Agric. Biol. 7(2): 50–54.*
Glazurina, et al., 1977, "Use of the Method of Artificial Mutagenesis in the Breeding of Flower Crops", Cytology and Genetics, vol. 11(3):42–45.*
Das, et al., 1977, "Improvement of Some Vegetatively Propagated Ornamentals by Gamma Radiation", Indian J. Horticulture, 34(2): 169–174.*
Dowrick, et al., 1966, "The Induction of Mutations in Chrysanthemum Using X– and Gamma Radiation", Euphytica, 15:204–210.*
Broertjes, 1966, Mutation Breeding of Chrysanthemum, Euphytica, 15:156–162.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Honey Yogilroy', characterized by its upright, outwardly spreading and uniformly mounded plant habit; compact growth habit; strong, dark green foliage; uniform flowering; early flowering; eight-week response time; large decorative-type inflorescences that are about 10 cm in diameter; light honey bronze-colored ray florets that may be more golden yellow under high temperatures; and good postproduction longevity with inflorescences and leaves maintaining good substance and color for about three weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Honey Yogilroy.

The new Chrysanthemum is a product of a mutation induction breeding program conducted by the Inventor in Fort Myers, Fla., and Salinas, Calif. The objective of the program is to create new Chrysanthemum cultivars with desirable inflorescence form and floret colors, good substance, and excellent post-production longevity.

The new Chrysanthemum originated by exposing unrooted cuttings of the Chrysanthemum cultivar Gilroy, disclosed in U.S. Plant Pat. No. 10,252 to gamma-ray radiation at a level of 2,000 rads in September, 1995, in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Salinas, Calif. The new Chrysanthemum was discovered and selected by the Inventor as a single flowering plant within this population in April, 1996. The selection of this plant was based on its desirable inflorescence form and ray floret color.

Asexual reproduction of the new Chrysanthemum by terminal cuttings harvested in a controlled environment in Salinas, Calif., has shown that the unique features of this new Chrysanthemum are stable and reproduced true to type in successive generations.

Asexual reproduction of the new Chrysanthemum by terminal cuttings harvested in a controlled environment in Fort Myers, Fla., has shown that the unique features of this new Chrysanthemum are stable and reproduced true to type in successive generations.

SUMMARY OF THE INVENTION

The cultivar Honey Yogilroy has not been observed under all possible environment conditions. The phenotype may vary somewhat with variations in environment such as temperature, daylength and light intensity, without, however, any variance in genotype.

The following traits have been repeatedly observed and are determined to be the unique characteristics of 'Honey Yogilroy'. These characteristics in combination distinguish 'Honey Yogilroy' as a new and distinct Chrysanthemum:

1. Upright, outwardly spreading and uniformly mounded plant habit.

2. Compact growth habit.

3. Strong, dark green foliage.

4. Uniform flowering.

5. Early flowering, eight-week response time.

6. Large decorative-type inflorescences that are about 10.1 cm in diameter.

7. Light honey bronze-colored ray florets that may be more golden yellow under high day temperatures, that is, at temperatures above 27° C.

8. Good postproduction longevity with inflorescences and leaves maintaining good substance and color for about three weeks in an interior environment.

Compared to plants of the parent cultivar, Gilroy, plants of the new Chrysanthemum have lighter colored ray florets. Additionally, inflorescences of the new Chrysanthemum are more reflexed than inflorescences of the parent cultivar, Gilroy.

BRIEF DESCRIPTION OF THE PHOTOGRAPHS

The accompanying colored photographs illustrate and overall appearance of the new Chrysanthemum showing the colors as true as it is reasonably possible to obtain in colored reproductions of this type.

The photograph at the top of the first sheet comprises a top perspective view of a typical flowering plant of 'Honey Yogilroy'.

The photograph at the bottom of the first sheet comprises a close-up view of a typical inflorescence and upper (left) and lower (right) surfaces of typical leaves of the cultivar Honey Yogilroy.

The photograph at the top of the second sheet comprises a side perspective view of typical flowering plants of 'Honey Yogilroy' (left) and 'Gilroy' (right).

The photograph at the bottom of the second sheet comprises a close-up view of typical inflorescences of plants of 'Honey Yogilroy' (left) and 'Gilroy' (right). Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., and Leamington, Ontario, Canada, under greenhouse conditions which approximate those generally used in commercial potted Chrysanthemum production. Four unrooted cuttings were directly stuck in a 15-cm container and pinched once. Plants used for this description were grown as disbudded-types. Measurements and numerical values represent averages of typical flowering plants.

Botanical classification: *Dendranthema grandiflora* cultivar Honey Yogilroy.

Commercial classification: Decorative disbudded-type pot Chrysanthemum.

Parentage: Induced mutation of the *Dendranthema grandiflora* cultivar Gilroy, disclosed in U.S. Plant Pat. No. 10,252.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous decorative pot Chrysanthemum typically grown as a disbudded-type. Inverted triangle; compact, stems mostly upright and outwardly spreading giving a uniformly mounded appearance to the plant. Freely branching; about three or four lateral branches develop after removal of terminal apex (pinching); dense and full plants.

*Plant height.*—Compact, about 23 cm.

*Plant width.*—About 36 cm.

*Stem color.*—Greener than 147B.

*Stem texture.*—Pubescent.

*Foliage description.*—Arrangement: Alternate. Length: About 8.6 cm. Width: About 6.1 cm. Apex: Cuspidate to mucronate. Base: Attenuate. Margin: Palmately lobed, sinuses between lateral lobes parallel to divergent. Texture: Upper and lower surfaces with very fine pubescence; veins prominent on lower surface. Petiole length: About 2.2 cm. Color: Young foliage upper surface: Darker than 147A. Young foliage lower surface: Close to 147B. Mature foliage upper surface: Darker than 147A. Mature foliage lower surface: Close to 147B. Venation upper surface: 147A to 147B. Venation lower surface: 147B.

Inflorescence description:

*Appearance.*—Decorative inflorescence form with elongated oblong-shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later.

*Postproduction longevity.*—Inflorescences and leaves will maintain good color and substance for about three weeks in an interior environment.

*Quantity of inflorescences.*—As a disbudded-type, all lateral inflorescences are removed to allow for maximum terminal inflorescnece size. One inflorescence per lateral stem; about three or four inflorescenecs per plant.

*Inflorescence bud.*—Height: About 7 mm. Diameter: About 8 mm. Color: Close to 143A.

*Inflorescence size.*—Diameter: About 10.1 cm. Depth (height): About 3.5 cm. Diameter of disc: About 6 mm, inconspicuous.

*Ray florets.*—Shape: Elongated, oblong. Orientation: Initially upright, incurved, then perpendicular to peduncle to reflexed. Aspect: Initially incurved. Length: About 5.7 cm. Width: About 1.4 cm. Apex: Pointed to emarginate. Margin: Entire. Texture: Iridescent, satiny; longitudinally ridged. Number of ray florets per inflorescence: Numerous about 205. Color: When opening: Yellow, 5A. Fully opened, upper surface: Honey bronze, close to 12A overlain with faint brownish orange, close to 167A to 167B, longitudinal streaks. Fully opened, lower surface: 8C to 10C.

*Disc florets.*—Shape: Tubular. Apex: Serrated. Length: About 5.5 mm. Width: Apex, about 1.5 mm; base, about 1 mm. Number of disc florets per inflorescence: Few, about 15. Color: Immature: 144A. Mature: Apex: 9A. Mid-section and base: White, 155D.

*Reproductive organs.*—Androecium: Present on disc florets only. Anther color: 9A. Pollen amount: Scarce. Pollen color: 14A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Honey Yogilroy', as illustrated and described.

* * * * *

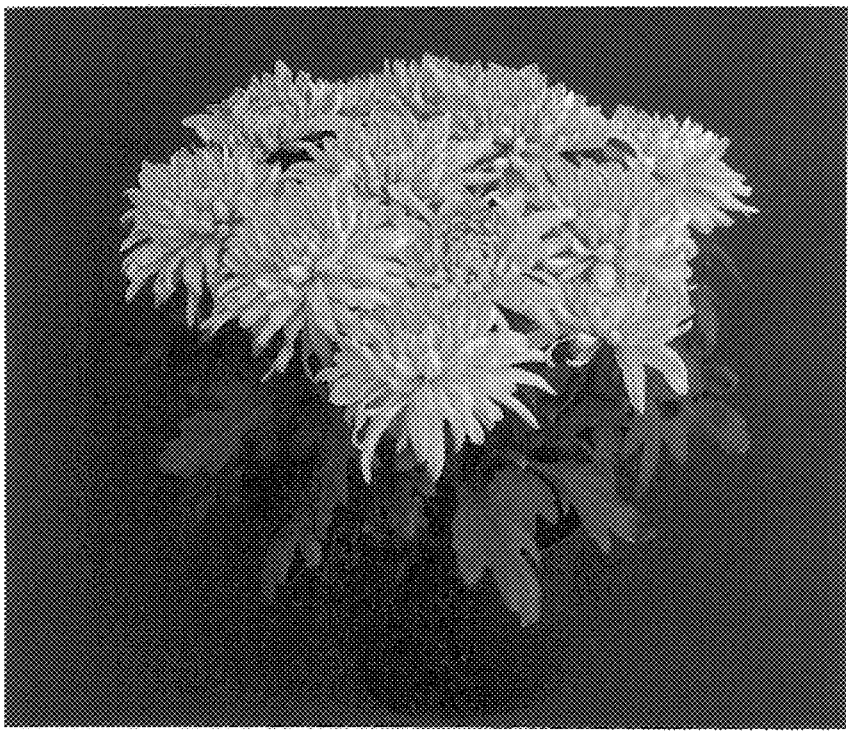
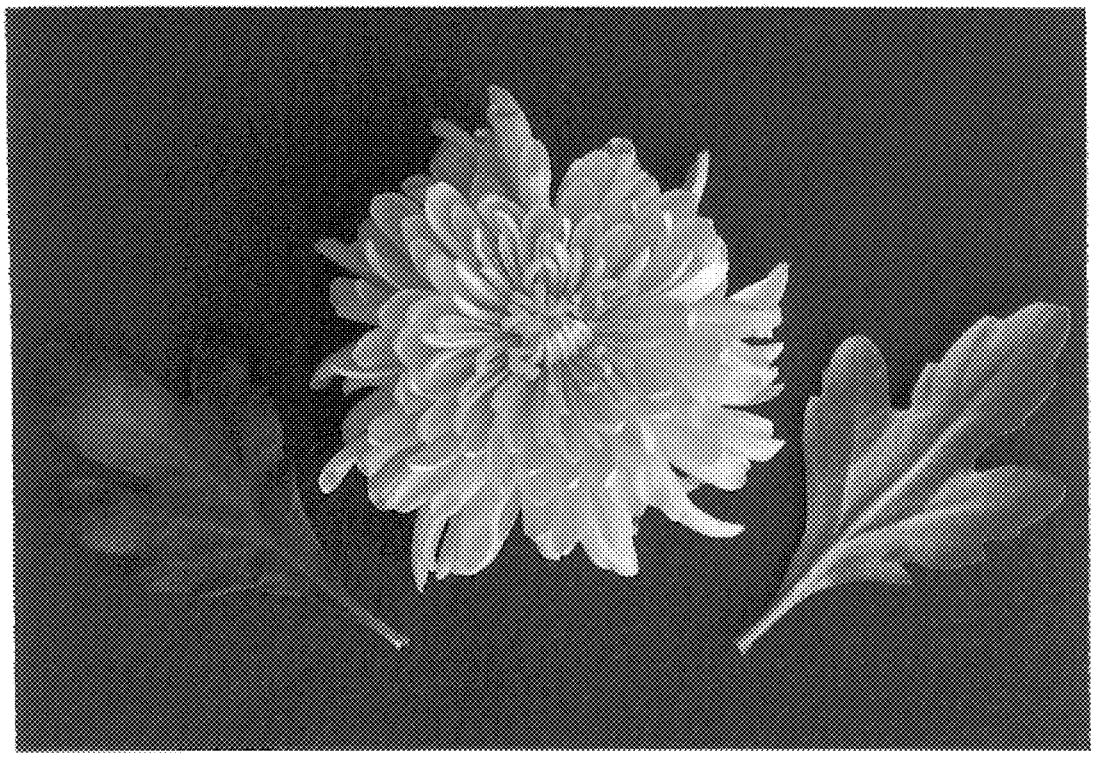

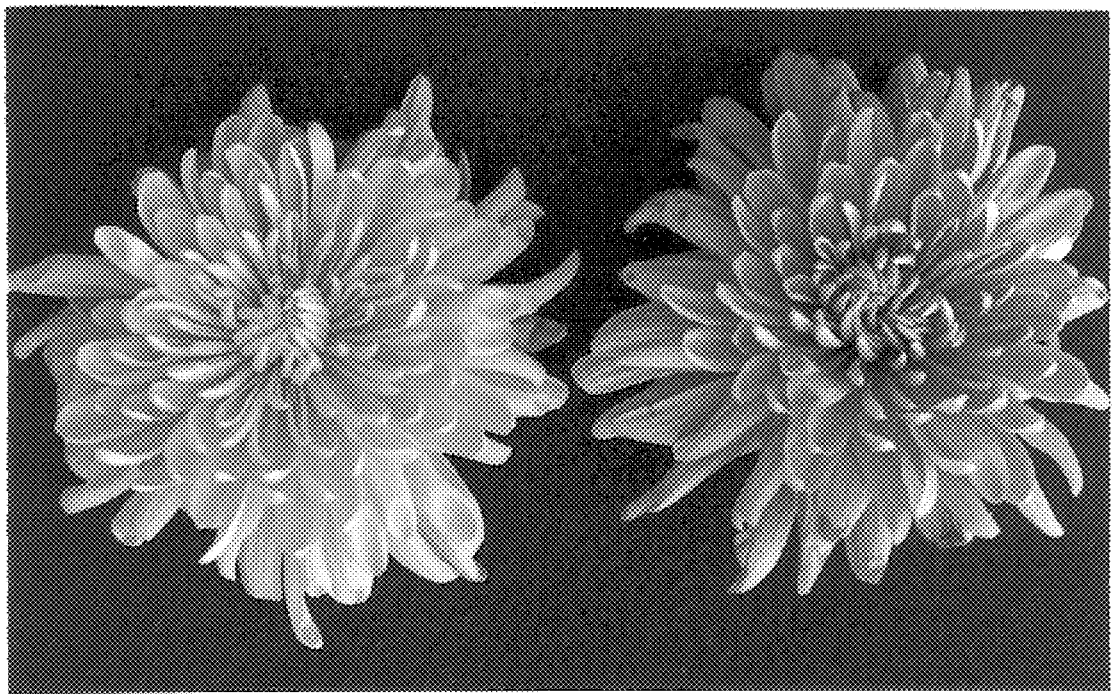

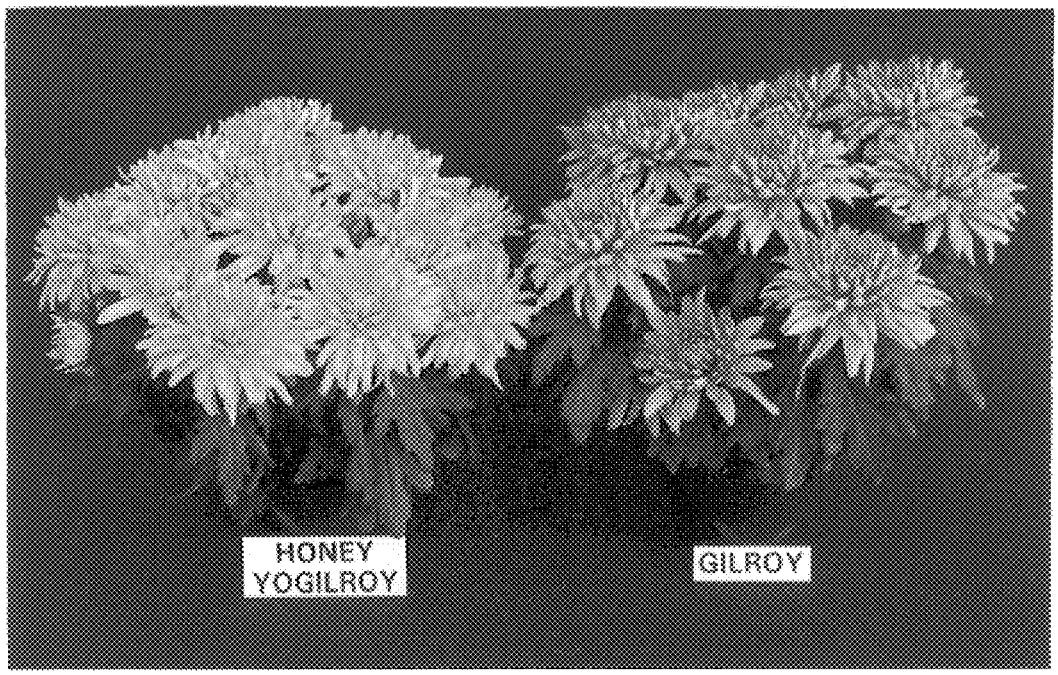
HONEY
YOGILROY
GILROY